US010420691B2

(12) United States Patent
Stewart

(10) Patent No.: US 10,420,691 B2
(45) Date of Patent: Sep. 24, 2019

(54) KNEE RANGE OF MOTION DEVICE UTILIZING TANGENTIAL JOINT TRANSLATION AND DISTRACTION

(71) Applicant: Richard Stewart, Mooresville, NC (US)

(72) Inventor: Richard Stewart, Mooresville, NC (US)

( * ) Notice: Subject to any disclaimer, the term of this patent is extended or adjusted under 35 U.S.C. 154(b) by 388 days.

(21) Appl. No.: 15/440,022

(22) Filed: Feb. 23, 2017

(65) Prior Publication Data

US 2017/0239119 A1 Aug. 24, 2017

Related U.S. Application Data

(60) Provisional application No. 62/299,169, filed on Feb. 24, 2016.

(51) Int. Cl.
*A61G 13/12* (2006.01)
*A61H 1/02* (2006.01)
(Continued)

(52) U.S. Cl.
CPC ............ *A61G 13/1245* (2013.01); *A61F 5/00* (2013.01); *A61G 13/02* (2013.01); *A61H 1/024* (2013.01);
(Continued)

(58) Field of Classification Search
CPC ... A61G 13/1245; A61G 13/125; A61H 1/024
See application file for complete search history.

(56) References Cited

U.S. PATENT DOCUMENTS 2,058,563 A 12/1934 Campbell
2,720,396 A * 10/1955 Pfaus ............... A63B 23/03533
482/130

(Continued)

FOREIGN PATENT DOCUMENTS

RU 94037625 9/1996

OTHER PUBLICATIONS

Mohd Azuwan Mar Dzahir et al. Recent Trends in Lower-Limb Robotic Rehabilitation Orthosis: Control Scheme and Strategy for Pneumatic Muscle Actuated Gait Trainers, Robotics 2014, 3, 120-148, Basel, Switzerland.

*Primary Examiner* — Eric J Kurilla
(74) *Attorney, Agent, or Firm* — Trego, Hines & Ladenheim, PLLC; Brandon Trego; Jonathan Hines

(57) ABSTRACT

A knee range of motion device utilizing tangential joint translation and distraction is disclosed. The device includes a carriage connected to a base, the carriage having a base attachment section; a thigh support section pivotally attached to the base attachment section; and a lower leg support section pivotally connected to the thigh support section. The device further including a carriage support extending between the thigh support section and the base, the carriage support pivotally connected to the thigh support section and adapted to slide in slots on the base; a first actuator connected to the lower leg support section to extend and retract the lower leg support section, thereby causing a foot support connected to the lower leg section to move; and a second actuator connected to the lower leg support section to raise and lower a calf support, causing an anterior and posterior tibial translation.

19 Claims, 4 Drawing Sheets

(51) Int. Cl.
*A61G 13/02* (2006.01)
*A61F 5/00* (2006.01)

(52) U.S. Cl.
CPC ........ *A61G 2210/00* (2013.01); *A61H 1/0244* (2013.01); *A61H 1/0266* (2013.01); *A61H 2201/0192* (2013.01); *A61H 2201/1207* (2013.01); *A61H 2201/1246* (2013.01); *A61H 2201/1642* (2013.01); *A61H 2201/1664* (2013.01); *A61H 2201/1676* (2013.01); *A61H 2201/50* (2013.01); *A61H 2201/5035* (2013.01); *A61H 2201/5097* (2013.01)

(56) References Cited

U.S. PATENT DOCUMENTS

| | | | |
|---|---|---|---|
| 4,474,176 A | 10/1984 | Farris et al. | |
| 4,492,222 A | 1/1985 | Hajanpour | |
| 4,558,692 A | 12/1985 | Greiner | |
| 4,566,440 A | 1/1986 | Berner et al. | |
| 4,603,687 A | 8/1986 | Greenwood | |
| 4,751,917 A | 6/1988 | Ruf | |
| 4,834,073 A | 5/1989 | Bledsoe et al. | |
| 5,020,797 A | 6/1991 | Burns | |
| 5,122,106 A * | 6/1992 | Atwood | A61H 1/0244 482/131 |
| 5,303,716 A | 4/1994 | Mason et al. | |
| 5,333,604 A | 8/1994 | Green et al. | |
| 5,901,581 A | 5/1999 | Chen et al. | |
| 6,102,882 A | 8/2000 | Cobo | |
| 6,221,032 B1 * | 4/2001 | Blanchard | A61H 1/024 601/23 |
| 6,416,448 B1 * | 7/2002 | Hassler | A61H 1/024 482/113 |
| 6,921,403 B2 | 7/2005 | Cragg et al. | |
| 7,309,320 B2 | 12/2007 | Schmehl | |
| 7,632,310 B2 | 12/2009 | Clifford et al. | |
| 7,695,416 B2 | 4/2010 | Weiner | |
| 7,998,046 B2 | 8/2011 | Johnson | |
| 8,058,823 B2 | 11/2011 | Horst et al. | |
| 8,060,210 B1 | 11/2011 | Carroll | |
| 8,066,656 B2 | 11/2011 | Bonutti et al. | |
| 8,346,367 B2 | 1/2013 | Carroll | |
| 8,579,771 B2 | 11/2013 | Rastegar et al. | |
| 8,805,662 B2 | 8/2014 | White | |
| 9,033,992 B2 | 5/2015 | Boudreault et al. | |
| 9,107,794 B2 | 8/2015 | Ewing | |
| 9,125,789 B2 | 8/2015 | Garcia | |
| 2006/0116246 A1 * | 6/2006 | Hankin | A61H 1/003 482/51 |
| 2006/0142680 A1 | 6/2006 | Iarocci | |
| 2007/0100267 A1 | 5/2007 | Bonutti et al. | |
| 2007/0161479 A1 | 7/2007 | Harris | |
| 2008/0119765 A1 | 5/2008 | Meckel et al. | |
| 2009/0093353 A1 | 4/2009 | Weiner | |
| 2009/0163837 A1 | 6/2009 | Sanger et al. | |
| 2009/0197741 A1 | 8/2009 | Poillucci et al. | |
| 2010/0192961 A1 * | 8/2010 | Amiot | A61G 13/12 128/882 |
| 2010/0313897 A1 | 12/2010 | Schaeffer | |
| 2011/0160625 A1 | 6/2011 | Yefimov | |
| 2012/0065030 A1 * | 3/2012 | Sandvig | A63B 21/0442 482/79 |
| 2012/0209156 A1 * | 8/2012 | Leismer | A61H 1/024 601/49 |
| 2012/0232438 A1 | 9/2012 | Cataldi et al. | |
| 2012/0318278 A1 * | 12/2012 | Aboujaoude | A61G 13/0036 128/845 |
| 2013/0197403 A1 | 8/2013 | Sevy et al. | |
| 2014/0031728 A1 | 1/2014 | Guillen | |
| 2014/0088466 A1 * | 3/2014 | Hansen | A61H 1/008 601/34 |
| 2014/0094721 A1 * | 4/2014 | Diallo | A61H 1/024 601/5 |
| 2014/0228186 A1 | 8/2014 | Montgomery | |

* cited by examiner

KNEE RANGE OF MOTION DEVICE UTILIZING TANGENTIAL JOINT TRANSLATION AND DISTRACTION

BACKGROUND OF THE INVENTION

This invention relates generally to a knee range of motion device, and more particularly, to a knee range of motion device utilizing tangential joint translation and distraction to help individuals regain range of motion in their knee after joint arthroplasty or arthrofibrosis.

Joint arthroplasty is a procedure used to restore the function of a joint. Typically, joint arthroplasty is used to relieve joint pain and disability which are caused by arthritis or a degenerative joint disease. The procedure may include a resurfacing of the bones at the joint, a partial replacement of the joint, or even a full replacement of the joint. One of the most common joint arthroplasty procedures is performed on the knee, i.e. knee replacement surgery.

Stiffness of the knee joint following joint arthroplasty is a common problem. People can develop scar tissue adhesions which can limit their knee range of motion and ultimately their functional activities. One way to reduce stiffness and combat scar tissue is to move the joint. Currently there are continuous passive motion devices, which act on a simple hinge moving the knee into flexion and extension. The knee however does not act purely as a hinge joint, but has translation along the joint surface. The knee joint can also become restricted by ligaments which may shorten, thereby necessitating joint distraction and mobilization to maintain their proper length.

Accordingly, there is a need for a continuous passive motion device configured to provide tibial translation and joint distraction.

BRIEF SUMMARY OF THE INVENTION

This need is addressed by the present invention, which provides a knee range of motion device configured to move the knee into flexion and extension as well as provide tibial translation and joint distraction.

According to one aspect of the invention, a knee range of motion device includes a carriage connected to a base, the carriage including a base attachment section connected to the base; a thigh support section pivotally connected to the base attachment section and configured to support a user's upper leg; and a lower leg support section pivotally connected to the thigh support section and configured to support a user's lower leg. The device further including a carriage support configured to support the carriage, the carriage support extending between the thigh support section and the base, the carriage support pivotally connected to the thigh support section and adapted to slide in slots on the base; a first actuator connected to the lower leg support section to extend and retract the lower leg support section, thereby causing a foot support connected to the lower leg section to move; and a second actuator connected to the lower leg support section to anteriorly and posteriorly glide a calf support.

According to another aspect of the invention, a knee range of motion device includes a carriage connected to a base, the carriage including a base attachment section configured to attach the carriage to the base; a thigh support section pivotally connected to the base attachment section, the thigh support section having a first and second spaced-apart thigh support members; and a lower leg support section pivotally connected to the thigh support section, the lower leg support section having first and second spaced-apart lower leg support members, each of the lower leg support members having an outer support member and an inner support member, wherein the first lower leg support member is pivotally connected to the first thigh support member and the second lower leg support member is pivotally connected to the second thigh support member. The device further including a foot support connected to the inner support member of the first and second spaced-apart lower leg support members; a carriage support configured to support the carriage, the carriage support pivotally connected to and extending between the thigh support section and the base; first and second pneumatic cylinders, the first pneumatic cylinder being operably connected to the inner support member of the first lower leg support member to move the inner support member in and out of the outer support member and the second pneumatic cylinder being operably connected to the inner support member of the second lower leg support member to move the inner support member in and out of the outer support member, thereby moving the foot support; and a calf support extending between the first and second lower leg support members and operably connected to third and fourth pneumatic cylinders, the third pneumatic cylinder being connected to a first end of the calf support and the fourth pneumatic cylinder being connected to a second end of the calf support such that the third and fourth pneumatic cylinders cause the calf support to move.

According to another aspect of the invention, a method of improving joint range of motion after surgery includes the steps of providing a joint motion device; using the device to move a user's joint between a pre-determined flexion position and a pre-determined extension position; prior to reaching the pre-determined flexion position, using the device to move the joint to provide joint distraction and retraction; at the pre-determined flexion position, using the device to move the joint in an oscillatory manner to provide joint translation; prior to reaching the pre-determined extension position, using the device to move the joint in an oscillatory manner to provide joint translation; and at the pre-determined extension position, using the device to move the joint in an oscillatory manner to provide joint distraction and retraction.

BRIEF DESCRIPTION OF THE DRAWINGS

The invention may be best understood by reference to the following description taken in conjunction with the accompanying drawing figures, in which.

DETAILED DESCRIPTION OF THE INVENTION

Figures 1, 2:
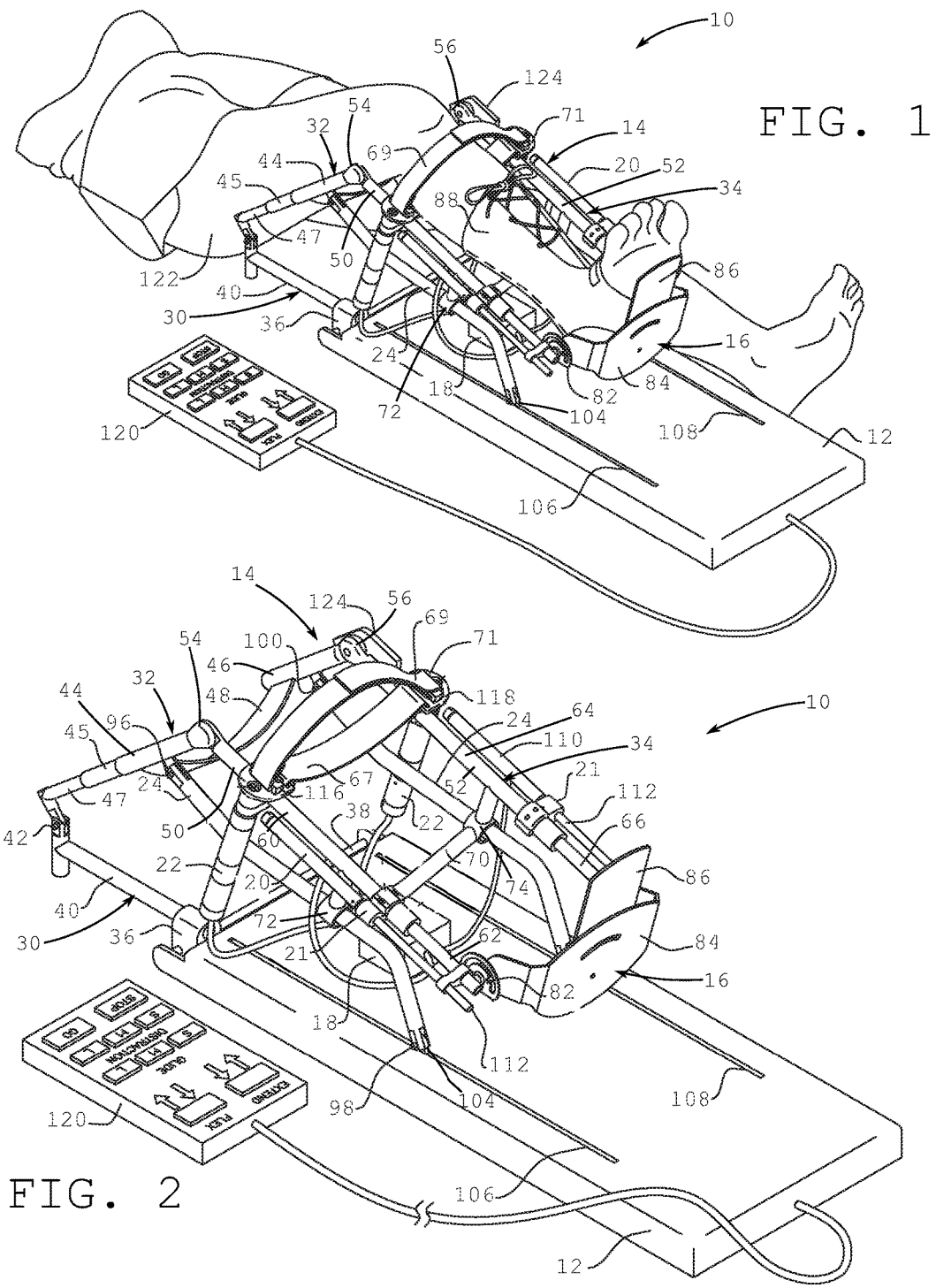
FIG. 1 is a perspective view of a user using a range of motion device.
FIG. 2 is another perspective view of the of the range of motion device.
Figure 3:
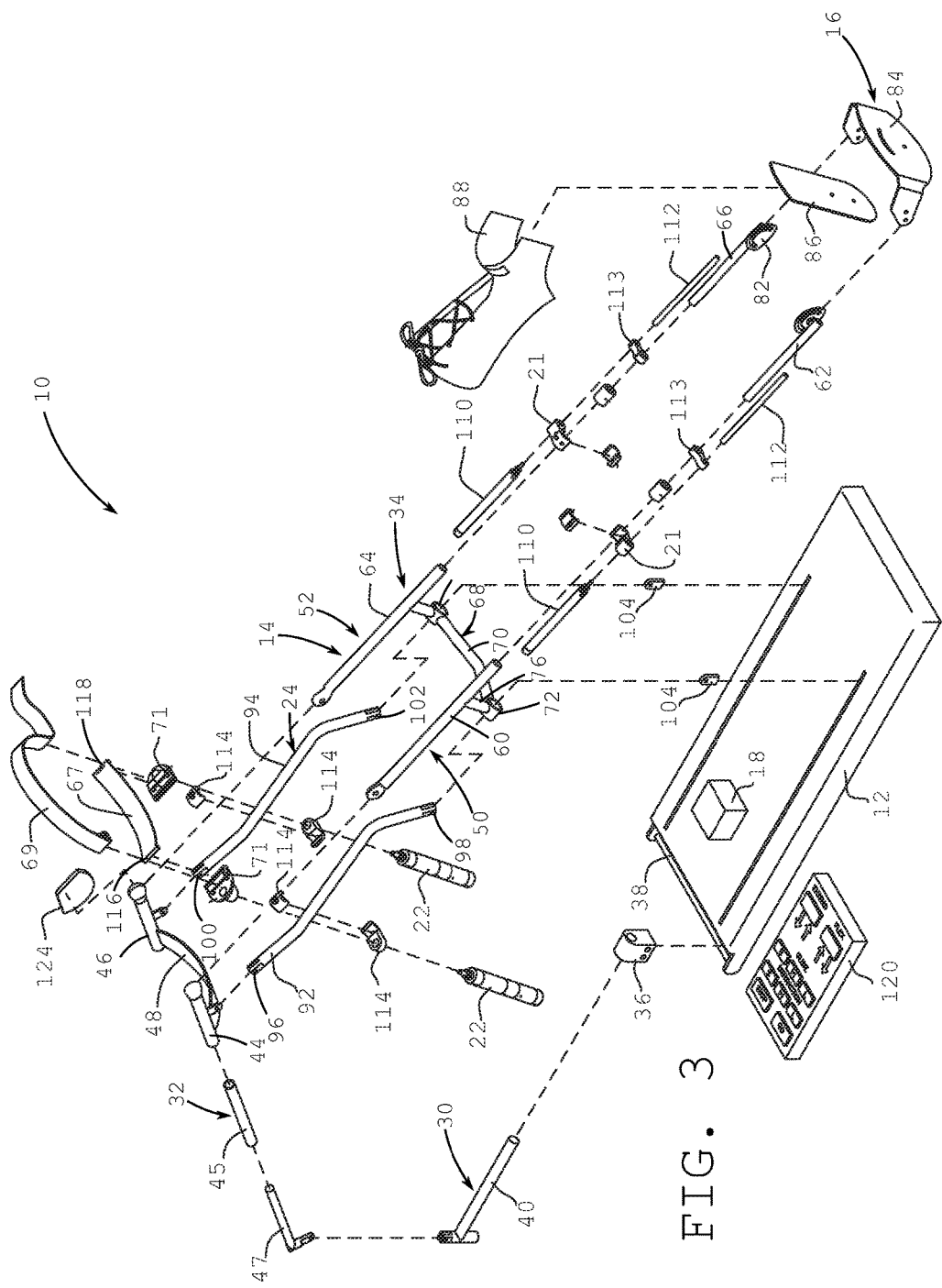
FIG. 3 is an exploded view of the range of motion device.
Figure 4:
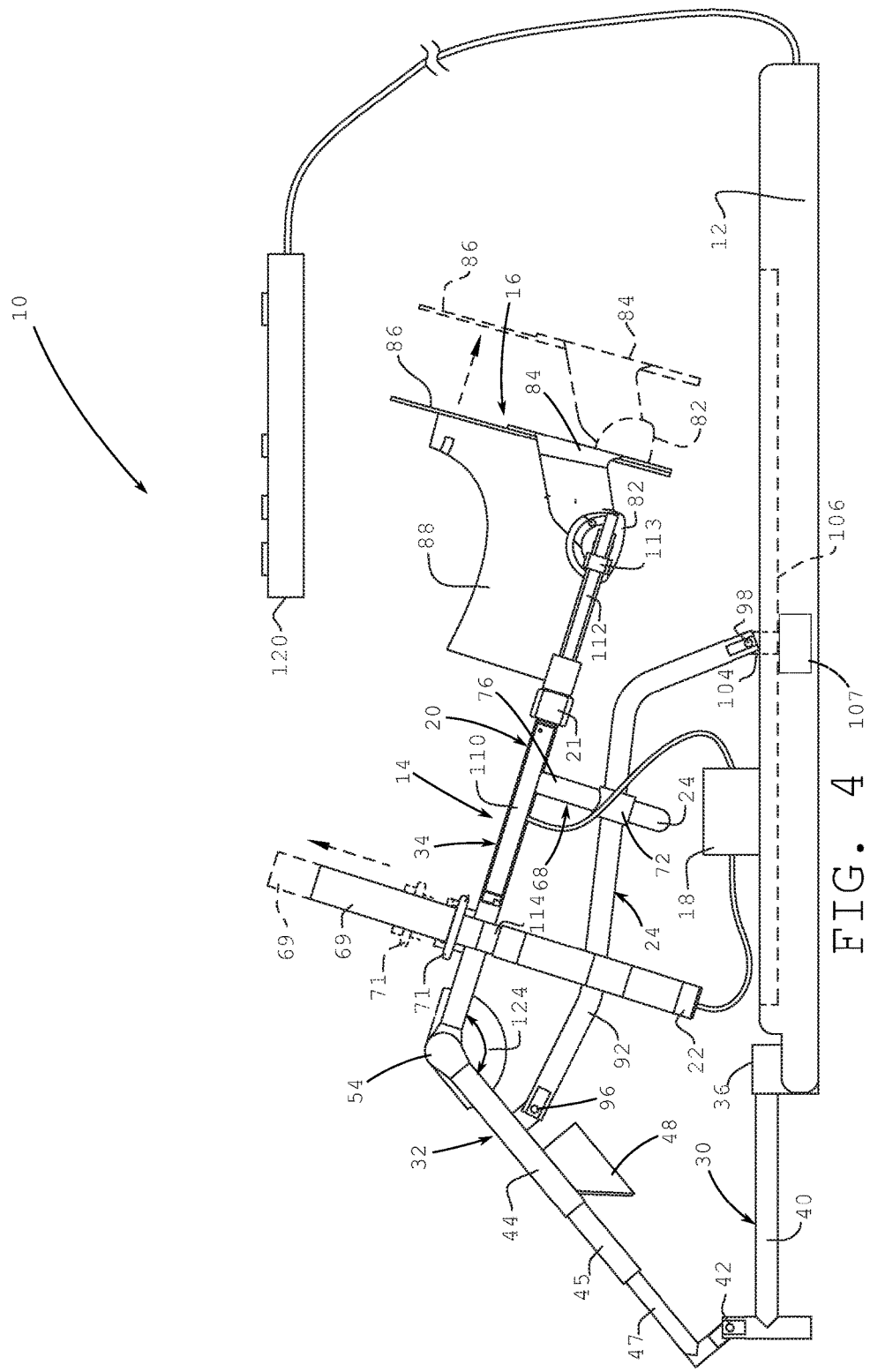
FIG. 4 is a side view of the range of motion device.
Figure 5:
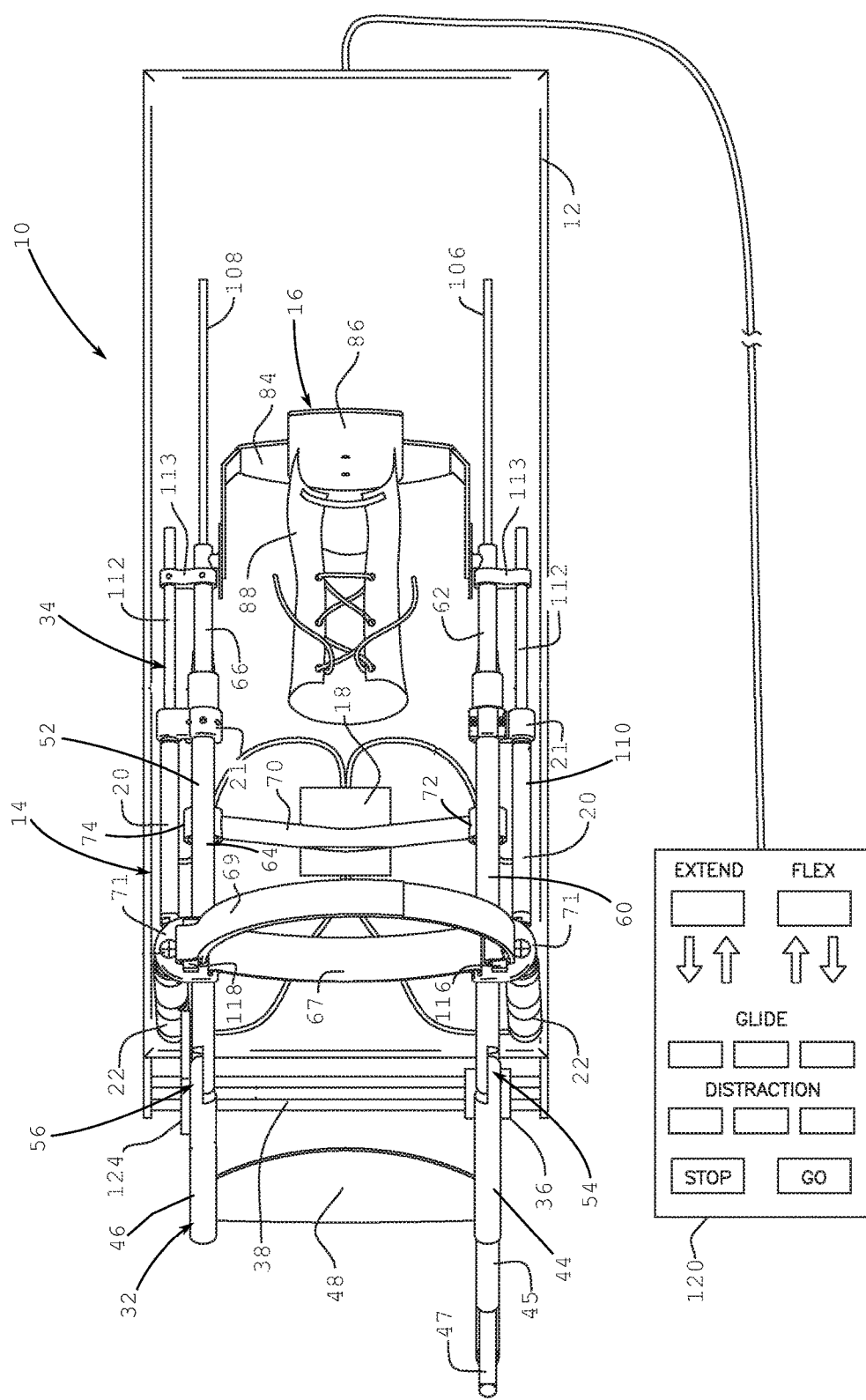
FIG. 5 is a top view of the range of motion device

Referring to the drawings wherein identical reference numerals denote the same elements throughout the various views, FIGS. 1-5 illustrate a knee range of motion device 10 utilizing tangential joint translation to aid an individual in gaining range of motion in their knee by using the concave on convex rule and femoral roll back mechanism and distraction to prevent tightening of collateral ligaments or joint capsule. These movements further improve synovial fluid lubrication of the joint.

The motion device 10 includes a base 12, a leg support or carriage 14 connected to the base 12, a footrest or foot support 16 connected to the carriage 14, an air compressor 18 connected to actuators such as pneumatic cylinders 20 and 22, and a slidable carriage support 24 interconnecting the carriage 14 and base 12.

The carriage 14 includes a base attachment section 30, a thigh support section 32, and a lower leg support section 34. The base attachment section 30 includes a clamp 36 adapted for sliding movement along rail 38 of the base 12 and a support member 40 extending outwardly therefrom. The clamp 36 allows a user to switch the location of the base attachment section 30 and lock it in place depending on which leg the user is treating. As shown, in FIG. 1, if the user is treating the right leg, then the base attachment section 30 is positioned along the right side of the base 12 so that support member 40 resides along the right hip 122 of the user.

The support member 40 is pivotally connected to the thigh support section 32 at pin 42. The leg being treated determines which side of the thigh support section 32 is pivotally connected to the support member 40. The thigh support section 32 includes first and second spaced-apart thigh support members 44 and 46 and a thigh support 48 extending therebetween. As shown, support member 40 is pivotally attached to support member 44. As illustrated, support member 44 is in a telescoping configuration (two inner support members 45 and 47 to provide extension) and support member 46 is not; however, it should be appreciated that either of the support members 44 and 46 may be telescoped for pivotal connection to the support member 40. The thigh support 48 provides a hammock-type support that rests against the user's posterior thigh, thereby comfortably supporting the upper leg. The thigh support 48 may be made of any suitable material for providing a strong, comfortable support to the upper leg such as leather, canvas, nylon, and plastics and/or metal covered in padding.

The lower leg support section 34 includes first and second spaced-apart lower leg support members 50 and 52 which are pivotally connected to the thigh support members 44 and 46 (support member 50 is pivotally connected to support member 44 at joint 54 and support member 52 is pivotally connected to support member 46 at joint 56). Joints 54 and 56 may be of any suitable configuration to permit the thigh support section 32 and lower leg support section 34 to move smoothly relative to each other. Lower leg support member 50 includes an outer support member 60 and an inner support member 62 that slides in and out of the outer support member 60 to allow the support member 50 to telescope. Lower leg support member 52 includes an outer support member 64 and an inner support member 66 that slides in and out of the outer support member 64 to allow the support member 52 to telescope. A calf support 67 extends between the outer support members 60 and 64 and includes a securing strap 69 to secure a user's leg thereto. As illustrated, the securing strap 69 uses Velcro to secure the user's leg; however, it should be appreciated that the securing strap 69 may use other suitable means to secure the user's leg, such as snaps, hooks, and/or belt type holes and prong arrangement.

A U-shaped proximal calf support 68 is supported by the outer support members 60 and 64 at a location between and below the outer support members 60 and 64. As illustrated, the proximal calf support 68 includes a support member 70 extending between a first support ring 72 and a second support ring 74. First support ring 72 is connected to outer support member 60 by connector 76 and second support ring 74 is connected to outer support member 64 by connector 78.

The foot support 16 is pivotally connected to the inner support members 62 and 66 by connectors 82. The foot support 16 includes a base 84, a moveable plate 86, and an ankle brace or strap 88 to strap a user's foot therein, thereby securing the foot to the foot support 16. As shown, the base 84 is pivotally connected to the connectors 82 at opposing ends of the base 84 and the moveable plate 86 is moveable with respect to the base 84.

The carriage support 24 extends between the thigh support section 32 and the base 12. As illustrated, the carriage support 24 is pivotally attached to the thigh support section 32 and slidably connected to the base 12. The carriage support 24 includes first and second spaced-apart carriage members 92 and 94. First carriage member 92 is pivotally connected to thigh support member 44 at a first end 96 of the first carriage member 92, extends through first support ring 72, and is slidably connected to the base 12 at a second end 98. Second carriage member 94 is pivotally connected to thigh support member 46 at a first end 100, extends through second support ring 74, and is slidably connected to the base 12 at a second end 102. As shown, the first and second carriage members 92 and 94 are connected to sliding mechanisms 104 that slide and/or ride in slots 106 and 108 of the base 12. A drive mechanism 107 (such as a motor and drive screw) causes the sliding mechanisms 104 to move. Movement of the carriage support 24 causes the thigh support section 32 and leg support section 34 to move relative to each other, for example, such movement changes an angle $\theta$ between the thigh support section 32 and the leg support section 34.

Pneumatic cylinders 20 are supported by outer support members 60 and 64 (as shown, a single cylinder 20 is supported by outer support member 60 and a single cylinder is supported by outer support member 64 using connector 21, it should be appreciated that any suitable number of cylinders may be deployed). The pneumatic cylinders 20 each include an air cylinder 110 and a piston rod 112 moveable inward and outward from the cylinder 110. As illustrated, the piston rods 112 are connected to the inner support members 62 and 66 by connector 113 and are used to slide the inner and outer support members 62 and 66 in and out of the outer support members 60 and 64. Pneumatic cylinders 22 are three position pneumatic cylinders which are connected to the outer support members 60 and 64 (a single cylinder 22 is secured to each outer member 60 or 64) by bracket 114. Opposing ends 116 and 118 of the calf support 67 and securing strap 69 are secured to respective strap brackets 71 which are secured to the three position pneumatic cylinders 22 to permit the cylinders 22 to move a user's leg in translation, see FIG. 4.

The pneumatic cylinders 20 and 22 are connected to air compressor 18. Air compressor 18 and base 12 are operably connected to controller 120. As shown, the controller 120 is connected via a wired connection; however, it should be appreciated that the controller 120 may be connected wirelessly.

In use, a user sets up the motion device 10 for the desired leg to be moved by positioning the base attachment section 30 on the right or left side of the base 12 and uses clamp 36 to secure it in position. The user then connects the base attachment section 30 to the thigh support section 32 (as shown in FIG. 1, the base attachment section 30 is attached to thigh support member 44). The user then positions the leg in the motion device 10 by placing the base attachment section 30 along the user's hip 122, resting the user's posterior thigh on the thigh support 48, resting the user's calf on the calf support 67 and securing the leg thereto using the securing strap 69, and resting the user's foot on the foot support 16 and securing the foot thereto using the strap 88.

With the user's leg positioned and secured in the motion device 10, the user uses the controller 120 to move the user's leg. The user may move the leg from a bent position to an extended position (flexion and extension) and back by causing the carriage support 24 to move along the base 12 in slots 106 and 108, thereby causing the angle θ to move between about 65 degrees and about 183 degrees which corresponds to an hyper extension angle of about 3 degrees to a flexion angle of about 115 degrees. It should be appreciated that the angle θ and/or angle of flexion and extension may be increased, for example, the angle of flexion may be increased to about 130 degrees. A sensor 124 measures the angle of flexion and extension. As flexion increases to an adjustable end-range, the speed of flexion will slow and initiate joint distraction using cylinders 20 at a pre-determined cycle. For example, the cycle may include distracting the joint for about 5 seconds, relaxing the joint for about 1-2 seconds, and repeating distraction and resting for 3-5 cycles which will cause both distraction and retraction of the joint. Subsequent to the cylinder 20 deactivating, cylinders 22 are activated to provide joint translation at a rate of 20 oscillations/minute for 5 oscillations. As the joint returns to end-range extension, the cylinders 22 will again provide joint translation at about 3 degrees short of end-range extension at about 20 oscillations/minute. At end-range extension, the cylinders 20 again provide joint distraction for a pre-determined amount of time (20-40 seconds, preferably 30 seconds). This cycle is then repeated. It should be appreciated that the term "end-range" refers to a limit and/or stopping point at which the carriage support 24 stops moving along the slots 106, 108 in a flexion direction and an extension direction. This limit corresponds to the angle of flexion and extension measured by the sensor 124. This end-range is adjustable by the user prior to (i.e., pre-determined) using the device 10.

The foregoing has described a knee range of motion device utilizing tangential joint translation and distraction. All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

I claim:

1. A knee range of motion device, comprising:
   (a) a carriage connected to a base, the carriage comprising:
       (i) a base attachment section connected to the base;
       (ii) a thigh support section pivotally connected to the base attachment section and configured to support a user's upper leg; and
       (iii) a lower leg support section pivotally connected to the thigh support section and configured to support a user's lower leg;
   (b) a carriage support configured to support the carriage, the carriage support extending between the thigh support section and the base, the carriage support pivotally connected to the thigh support section and adapted to slide in slots on the base;
   (c) a first actuator connected to the lower leg support section to distract and retract the lower leg support section, thereby causing a foot support connected to the lower leg section to move; and
   (d) a second actuator connected to the lower leg support section to anteriorly and posteriorly glide a calf support.

2. The device according to claim 1, wherein the lower leg support section includes first and second spaced-apart lower leg support members, each of the lower leg support members having an outer support member and an inner support member configured to slide in and out of the outer support member.

3. The device according to claim 2, wherein the foot support is connected to the inner support member.

4. The device according to claim 2, wherein the calf support extends between the first and second lower leg support members and is connected to the second actuator.

5. The device according to claim 4, wherein the second actuator is connected to the lower leg support section at a location where the calf support is connected to the first and second lower leg support members.

6. The device according to claim 1, further including a controller to control movement of the device, the controller providing commands to cause:
   (a) the carriage support to slide along the slots of the base, thereby causing an angle between the thigh support section and lower leg section to increase or decrease;
   (b) the first actuator to distract or retract the lower leg support section; and
   (c) the second actuator to anteriorly and posteriorly glide the calf support device in an oscillatory manner.

7. A knee range of motion device, comprising:
   (a) a carriage connected to a base, the carriage including:
       (i) a base attachment section configured to attach the carriage to the base;
       (ii) a thigh support section pivotally connected to the base attachment section, the thigh support section having a first and second spaced-apart thigh support members; and
       (iii) a lower leg support section pivotally connected to the thigh support section, the lower leg support section having first and second spaced-apart lower leg support members, each of the lower leg support members having an outer support member and an inner support member, wherein the first lower leg support member is pivotally connected to the first thigh support member and the second lower leg support member is pivotally connected to the second thigh support member;
   (b) a foot support connected to the inner support member of the first and second spaced-apart lower leg support members;
   (c) a carriage support configured to support the carriage, the carriage support pivotally connected to and extending between the thigh support section and the base;
   (d) first and second pneumatic cylinders, the first pneumatic cylinder being operably connected to the inner support member of the first lower leg support member to move the inner support member in and out of the outer support member and the second pneumatic cylinder being operably connected to the inner support member of the second lower leg support member to move the inner support member in and out of the outer support member, thereby moving the foot support; and (e) a calf support extending between the first and second lower leg support members and operably connected to third and fourth pneumatic cylinders, the third pneumatic cylinder being connected to a first end of the calf support and the fourth pneumatic cylinder being connected to a second end of the calf support such that the third and fourth pneumatic cylinders cause the calf support to move.

8. The device according to claim 7, wherein the first and second pneumatic cylinders cause the foot support to move, thereby pulling and pushing a user's foot secured in the foot support to cause knee joint distraction.

9. The device according to claim 7, wherein the carriage support moves along slots in the base to cause the carriage to move from an extended position where a user's leg secured in the carriage is extended, to a retracted position where the user's leg is bent to cause knee joint flexion and extension.

10. The device according to claim 7, wherein the third and fourth pneumatic cylinders cause the calf support to move anteriorly and posteriorly in an oscillatory manner, thereby causing knee joint translation.

11. A method of using the device of claim 7 to improve a knee joint's range of motion, comprising:
    (a) moving the carriage support along slots in the base to move a user's leg between a pre-determined flexion position and a pre-determined extension position;
    (b) at or prior to reaching the pre-determined flexion position, using the first and second pneumatic cylinders to move the foot support in an oscillatory manner to provide joint distraction and retraction;
    (c) at the pre-determined flexion position, using the third and fourth pneumatic cylinders to move the calf support in an oscillatory manner to provide joint translation;
    (d) at or prior to reaching the pre-determined extension position, using the third and fourth pneumatic cylinders to move the calf support in an oscillatory manner to provide joint translation; and
    (e) at the pre-determined extension position, using the first and second pneumatic cylinders to move the foot support in an oscillatory manner to provide joint distraction and retraction.

12. A method of improving joint range of motion, comprising the steps of:
    (a) providing a joint motion device;
    (b) using the device to move a user's joint between a pre-determined flexion position and a pre-determined extension position;
    (c) at or prior to reaching the pre-determined flexion position, using the device to move the joint to provide joint distraction and retraction;
    (c) at the pre-determined flexion position, using the device to move the joint in an oscillatory manner to provide joint translation;
    (d) at or prior to reaching the pre-determined extension position, using the device to move the joint in an oscillatory manner to provide joint translation; and
    (e) at the pre-determined extension position, using the device to move the joint in an oscillatory manner to provide joint distraction and retraction.

13. The method according to claim 12, wherein the device includes a carriage connected to a base, the carriage configured to support a user's leg and includes a thigh support section and a lower leg support section.

14. The method according to claim 13, wherein a foot support is connected to the lower leg support section.

15. The method according to claim 14, wherein an actuator is operably connected to the foot support and causes the foot support to move in an oscillatory manner to provide distraction and retraction of the joint.

16. The method according to claim 13, wherein the device further includes a carriage support, the carriage support having a first end pivotally connected to the thigh support and a second end slidably connected to a slot in the base.

17. The method according to claim 16, wherein movement of the carriage support along the slot in the base causes the carriage to move between the flexion and extension positions, thereby providing joint flexion and extension.

18. The method according to claim 13, wherein a calf support is connected to the lower leg support section.

19. The method according to claim 18, wherein an actuator is connected to the calf support to cause the calf support to move in an oscillatory manner to provide joint translation.

\* \* \* \* \*